(12) United States Patent
Parks et al.

(10) Patent No.: US 11,219,367 B2
(45) Date of Patent: Jan. 11, 2022

(54) POSITIONING SYSTEM FOR OPHTHALMIC INSTRUMENT

(71) Applicant: Reichert, Inc., Depew, NY (US)

(72) Inventors: Scott W. Parks, East Amherst, NY (US); David G. Kelkenberg, Akron, NY (US); Russell J. Bonaventura, Williamsville, NY (US)

(73) Assignee: Reichert, Inc., Depew, NY (US)

( * ) Notice: Subject to any disclaimer, the term of this patent is extended or adjusted under 35 U.S.C. 154(b) by 184 days.

(21) Appl. No.: 16/777,252

(22) Filed: Jan. 30, 2020

(65) Prior Publication Data

US 2021/0235988 A1    Aug. 5, 2021

(51) Int. Cl.
*A61B 3/15* (2006.01)
*A61B 3/00* (2006.01)
*A61B 3/16* (2006.01)

(52) U.S. Cl.
CPC ............ *A61B 3/152* (2013.01); *A61B 3/0008* (2013.01); *A61B 3/0075* (2013.01); *A61B 3/16* (2013.01)

(58) Field of Classification Search
CPC ..... A61B 3/107; A61B 3/0025; A61B 3/1015; A61B 3/14; A61B 3/1005; A61B 3/103; A61B 3/0091; A61B 3/165; A61B 3/1035; A61B 3/0008; A61B 3/102; A61B 3/135; A61B 3/113; A61B 3/117; A61B 3/145; A61B 3/0041; A61B 3/024; A61B 3/10; A61B 3/1025; A61B 3/112; A61F 2009/00872; A61F 9/008; A61F 9/00804; A61F 2009/00882; A61F 2/1613; A61F 2009/00848; A61F 2009/0088; A61F 2009/00895; A61F 2240/002; A61F 2/1637; A61F 9/00827; A61F 9/013; A61F 2009/00844; A61F 2009/00853; A61F 2009/0087; A61F 2009/00889; A61F 2/142; A61F 2/16; A61F 9/007; A61F 9/00806;
(Continued)

(56) References Cited

U.S. PATENT DOCUMENTS 3,756,073 A    9/1973   Lavallee et al.
4,665,923 A    5/1987   Kobayashi
(Continued)

FOREIGN PATENT DOCUMENTS

WO    2020/053476 A1    3/2020

*Primary Examiner* — William R Alexander
*Assistant Examiner* — Sharrief I Broome
(74) *Attorney, Agent, or Firm* — Hodgson Russ LLP

(57) ABSTRACT

A spatially compact, lightweight positioning system for guiding an operator in positioning an ophthalmic instrument relative to an eye of a test subject has first and second light sources and an area detector spaced apart from a measurement axis of the instrument and from each other for providing positioning images which may be evaluated relative to stored calibration image information to determine current position of the instrument relative to the eye. The first and second light sources may fit within a lateral distance less than or equal to 25 mm. First and second illumination axes associated with the light sources may reside in a horizontal plane containing the measurement axis, and an observation axis of the area detector may reside in a vertical plane containing the measurement axis. The light sources and the area detector may be intersected by a plane which is normal to the measurement axis.

13 Claims, 11 Drawing Sheets

(58) Field of Classification Search
CPC ............... G01B 11/2513; G01B 11/25; G01B 9/02091; G01B 9/02004; G01B 9/02077; G01B 11/028; G01B 11/167; G01B 11/255; G01B 2290/65; G01B 2290/70; G01B 9/02027; G01B 9/0203; G01B 9/02039; G01B 9/02041; G01B 9/02068; G02C 2202/06; G02C 2202/22; G02C 7/028; G02C 7/047; G02C 7/02; G02C 7/027; G02C 7/04; G02C 13/00; G02C 13/003; G02C 2202/24; G02C 7/021
See application file for complete search history.

(56) References Cited

U.S. PATENT DOCUMENTS

| | | | |
|---|---|---|---|
| 4,817,620 A * | 4/1989 | Katsuragi | A61B 3/152 600/401 |
| 4,881,807 A | 11/1989 | Luce et al. | |
| 4,995,393 A | 2/1991 | Katsuragi et al. | |
| 5,301,004 A * | 4/1994 | Percival | G01M 11/0235 356/125 |
| 6,042,544 A | 3/2000 | Miwa et al. | |
| 6,361,495 B1 * | 3/2002 | Grolman | A61B 3/165 600/401 |
| 6,544,193 B2 | 4/2003 | Abreu | |
| 6,623,429 B2 | 9/2003 | Percival et al. | |
| 6,669,340 B2 | 12/2003 | Percival et al. | |
| 6,685,318 B2 | 2/2004 | Kohayakawa | |
| 6,749,302 B2 | 6/2004 | Percival et al. | |
| 6,945,650 B2 | 9/2005 | Beverly | |
| 7,478,908 B2 * | 1/2009 | Lai | A61B 3/0083 351/206 |
| 9,116,365 B2 | 8/2015 | Haddadi et al. | |
| 9,928,421 B2 | 3/2018 | Thomet et al. | |
| 2002/0036749 A1 * | 3/2002 | Isogai | A61F 9/00804 351/206 |
| 2003/0058405 A1 * | 3/2003 | Cornsweet | A61B 3/10 351/212 |
| 2003/0086060 A1 * | 5/2003 | Beverly | A61B 3/165 351/208 |
| 2003/0088169 A1 * | 5/2003 | Percival | A61B 3/0058 600/399 |
| 2013/0314668 A1 * | 11/2013 | Haddadi | A61B 5/6803 351/204 |
| 2015/0339511 A1 * | 11/2015 | Thomet | G06T 7/73 348/78 |
| 2017/0100033 A1 | 4/2017 | Sakurada | |
| 2018/0055358 A1 | 3/2018 | Nakajima | |

* cited by examiner

MANUAL MODE

AUTOMATIC MODE

POSITIONING SYSTEM FOR OPHTHALMIC INSTRUMENT

FIELD OF THE DISCLOSURE

The present disclosure relates to ophthalmic instruments which are positioned relative to an eye of a test subject by an operator as a prerequisite to measuring an ophthalmic parameter of the eye. For example, the present disclosure relates to rebound tonometers which utilize a disposable probe for contacting a cornea of the eye to measure intraocular pressure (IOP), and non-contact tonometers which utilize an air pulse to temporarily deform the cornea to measure IOP.

BACKGROUND OF THE DISCLOSURE

A rebound tonometer is an ophthalmic instrument that propels a movable measurement probe in a controlled manner along a measurement axis toward the cornea of an eye to measure intraocular pressure. During a measurement, the probe contacts the cornea, decelerates at a rate which depends on intraocular pressure, and then rebounds in a direction away from the cornea back toward the instrument housing. The rebound tonometer detects the motion of the measurement probe and determines intraocular pressure based on the detected motion of the probe. For example, the measurement probe may have a magnetized shaft that travels within a coil in the instrument housing. The coil may be energized momentarily to propel the probe toward the cornea by electromagnetic force, and then, after energizing current to the coil is shut off, a current may be induced in the coil by the moving probe to provide a detectable voltage signal representing velocity of the probe as a function of time. Alternatively, two coils may be provided, wherein one coil is used to propel the probe and the moving probe induces current in the other coil to provide a measurement voltage signal. The voltage signal may be recorded and processed to determine a measured IOP value.

Proper three-dimensional positioning of the rebound tonometer relative to the eye is an important factor for IOP measurement accuracy and repeatability. Immediately prior to propelling the probe to commence an IOP measurement, the rebound tonometer is ideally positioned by the operator such that the measurement axis intersects the corneal apex while the test subject gazes directly along the measurement axis (X-Y alignment), and a rounded tip of the measurement probe is located at predetermined working distance (Z distance) from the corneal surface. Although ideal three-dimensional positioning is impossible to achieve due to movement of the operator's hand holding the tonometer and/or movement of the test subject, three-dimensional positioning within an acceptable tolerance range relative to the ideal position is required to obtain a reliable measurement result.

A non-contact tonometer, also referred to as an air-puff tonometer, is another type of ophthalmic instrument for measuring IOP. Like a rebound tonometer, a non-contact tonometer may be hand-held and manually positioned by an operator. Non-contact tonometers have a three-dimensional positioning requirement similar to that described above for a rebound tonometer, except that a fluid discharge tube for discharging an air pulse toward the eye defines the measurement axis and working distance.

Known systems for guiding an operator in positioning an ophthalmic instrument relative to an eye of a test subject tend to be large and complex. As a result, a measurement head of the instrument is correspondingly large and obstructs the operator's direct sight lines to the test subject's face, making the instrument more difficult to position and increasing a risk that the operator may inadvertently contact the test subject's face or eye with the instrument. In addition to being large in size, the measurement head may be undesirably heavy. If the ophthalmic instrument is hand-held, this makes it more difficult for an operator to hold the ophthalmic instrument steady and in proper position as the measurement is taken.

What is needed is a spatially compact positioning system for an ophthalmic instrument whereby blockage of direct sight lines from the operator to the face of a patient is reduced. What is further needed is a lightweight positioning system for a hand-held ophthalmic instrument so that a measurement head of the instrument is not unduly heavy.

SUMMARY OF THE DISCLOSURE

The present disclosure provides a spatially compact, lightweight positioning system for guiding an operator in positioning an ophthalmic instrument relative to an eye of a test subject. The ophthalmic instrument may be, for example, a rebound tonometer which propels a probe along a measurement axis of the instrument toward the eye, or a non-contact tonometer which discharges a fluid pulse along a measurement axis of the instrument toward the eye.

An ophthalmic instrument incorporating the positioning system generally comprises first and second light sources, an area detector, signal processing electronics, a memory, and an image evaluation module. The first and second light sources and area detector are each spaced apart from the measurement axis of the ophthalmic instrument and from each other. The first and second light sources direct respective illumination beams along first and second illumination axes to the eye, and the area detector captures positioning images of the eye when the ophthalmic instrument is positioned near the eye in preparation for a measurement. Each positioning image includes a first source image corresponding to the first light source and a second source image corresponding to the second light source. The signal processing electronics are connected to the area detector for receiving a plurality of pixel signals representing the positioning image and converting the plurality of pixel signals to a digital positioning image.

The memory stores positioning calibration information corresponding to an ideal three-dimensional position of the ophthalmic instrument relative to a calibration eye, wherein the positioning calibration information is based on a calibration location of the first source image and a calibration location of the second source image in a calibration image captured by the area detector when the ophthalmic instrument is at the ideal three-dimensional position relative to the calibration eye.

The image evaluation module is configured to evaluate each digital positioning image to determine current positioning information corresponding to a current three-dimensional position of the ophthalmic instrument relative to the eye, wherein the current positioning information is based on a current location of the first source image and a current location of the second source image in the digital positioning image. The image evaluation module is further configured to compare the current positioning information with the positioning calibration information stored in the memory and compute a position difference representing a difference between the current three-dimensional position of the ophthalmic instrument relative to the eye and the ideal three-dimensional position of the ophthalmic instrument relative to the calibration eye.

The ophthalmic instrument may further comprise a display connected to the image evaluation module, and the image evaluation module may be further configured to generate a positioning icon representing the current three-dimensional position of the ophthalmic instrument relative to the eye, and to output the digital positioning image and the positioning icon to the display, wherein the digital positioning image and the positioning icon are superimposed to provide a positioning guidance image displayed on the display. The positioning icon may be scaled such that a size of the positioning icon is inversely proportional to a current working distance of the ophthalmic instrument from the eye along the measurement axis, and an appearance attribute (e.g. a color) of the positioning icon may be dependent upon whether or not the computed position difference is within a predetermined positioning tolerance for measurement purposes.

The ophthalmic instrument may also comprise a controller for initiating a measurement. The image evaluation module may be connected to the controller and may be further configured to send a position confirmation signal to the controller when the computed position difference is within a predetermined positioning tolerance, and the controller may automatically initiate the measurement in response to the position confirmation signal when the ophthalmic instrument is in an automatic measurement mode.

In a disclosed embodiment, the first and second light sources may fit within a lateral distance which is less than or equal to 25 mm. The first and second illumination axes may be coplanar with the measurement axis and form an angle which is bisected by the measurement axis. An observation axis of the area detector may be coplanar with the measurement axis. The first and second illumination axes may be arranged in a horizontal plane containing the measurement axis, and the observation axis may be arranged in a vertical plane containing the measurement axis. The first and second illumination axes may converge at a first point along the measurement axis within a field of view of the area detector, and the observation axis may intersect the measurement axis at a second point along the measurement axis spaced from the first point. The ophthalmic instrument may have a working distance reference point on the measurement axis, wherein a distance between the working distance reference point and the second point is greater than a distance between the working distance reference point and the first point. The first light source, the second light source, and the area detector may be intersected by a plane which is normal to the measurement axis of the ophthalmic instrument.

BRIEF DESCRIPTION OF THE DRAWING VIEWS

The nature and mode of operation of the present invention will now be more fully described in the following detailed description taken with the accompanying drawing figures, in which.

Figure 11A:
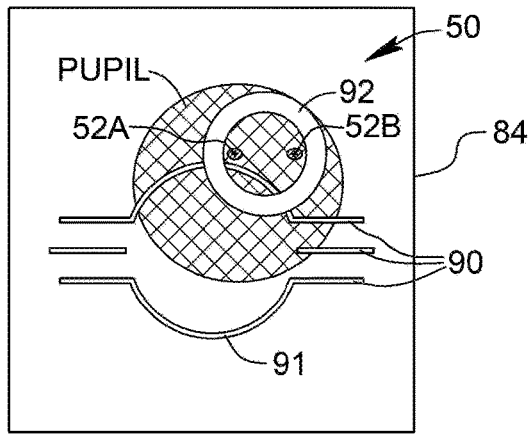
Figure 11B:
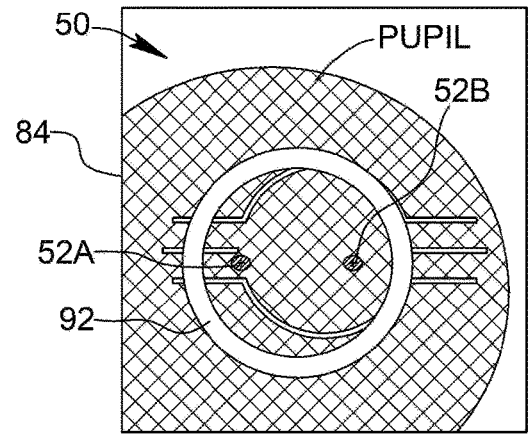
Figure 11C:
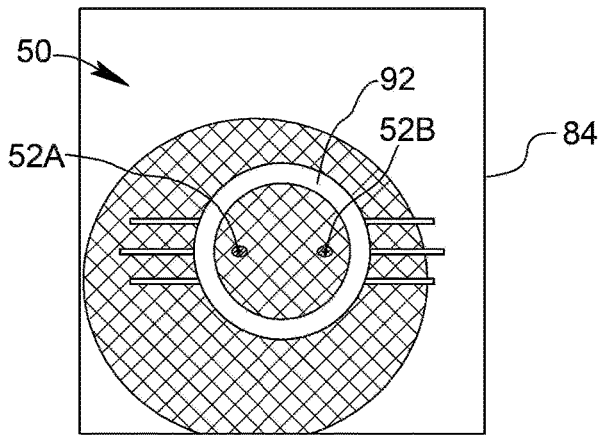
Figure 12:
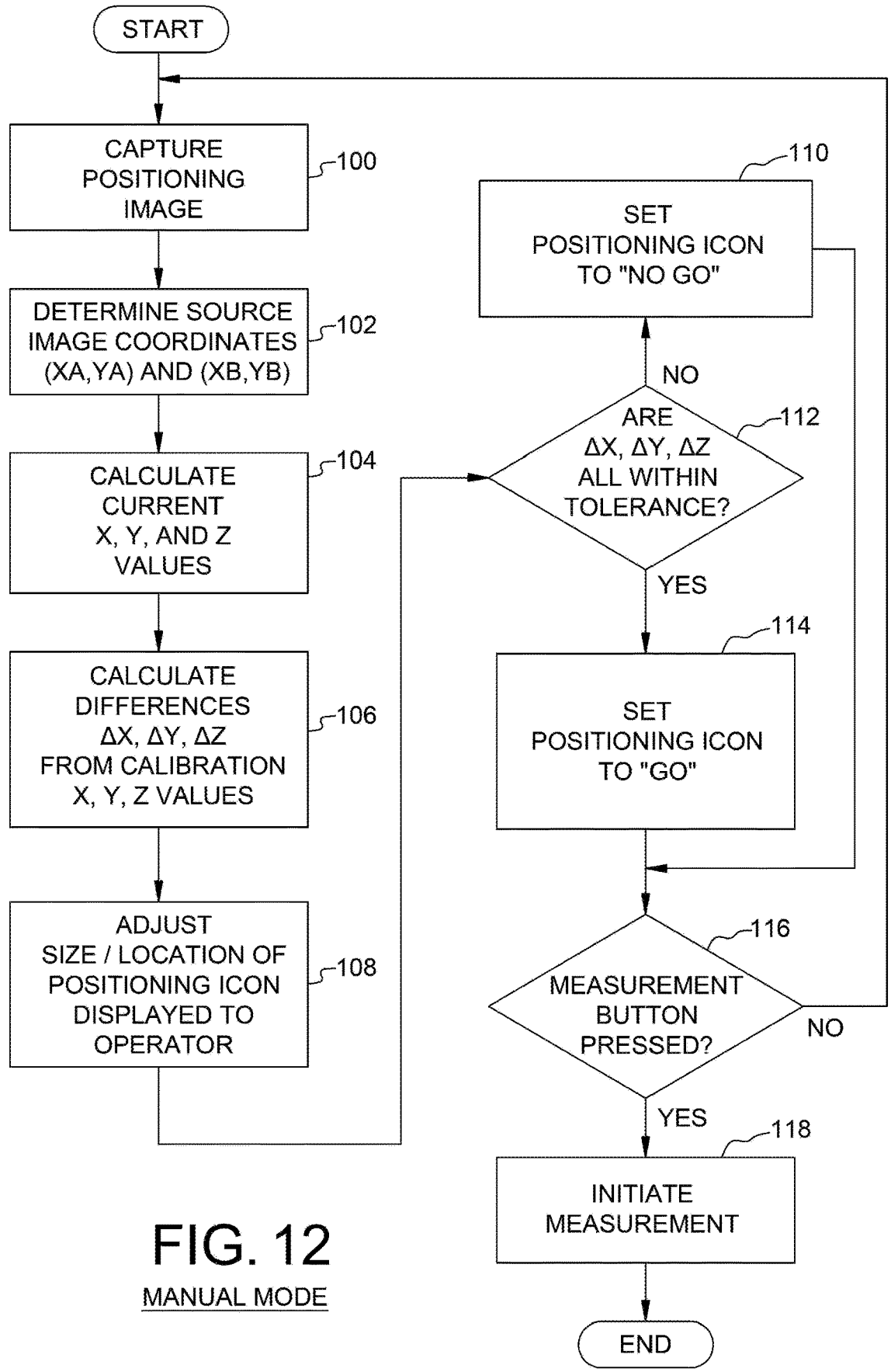
Figure 13:
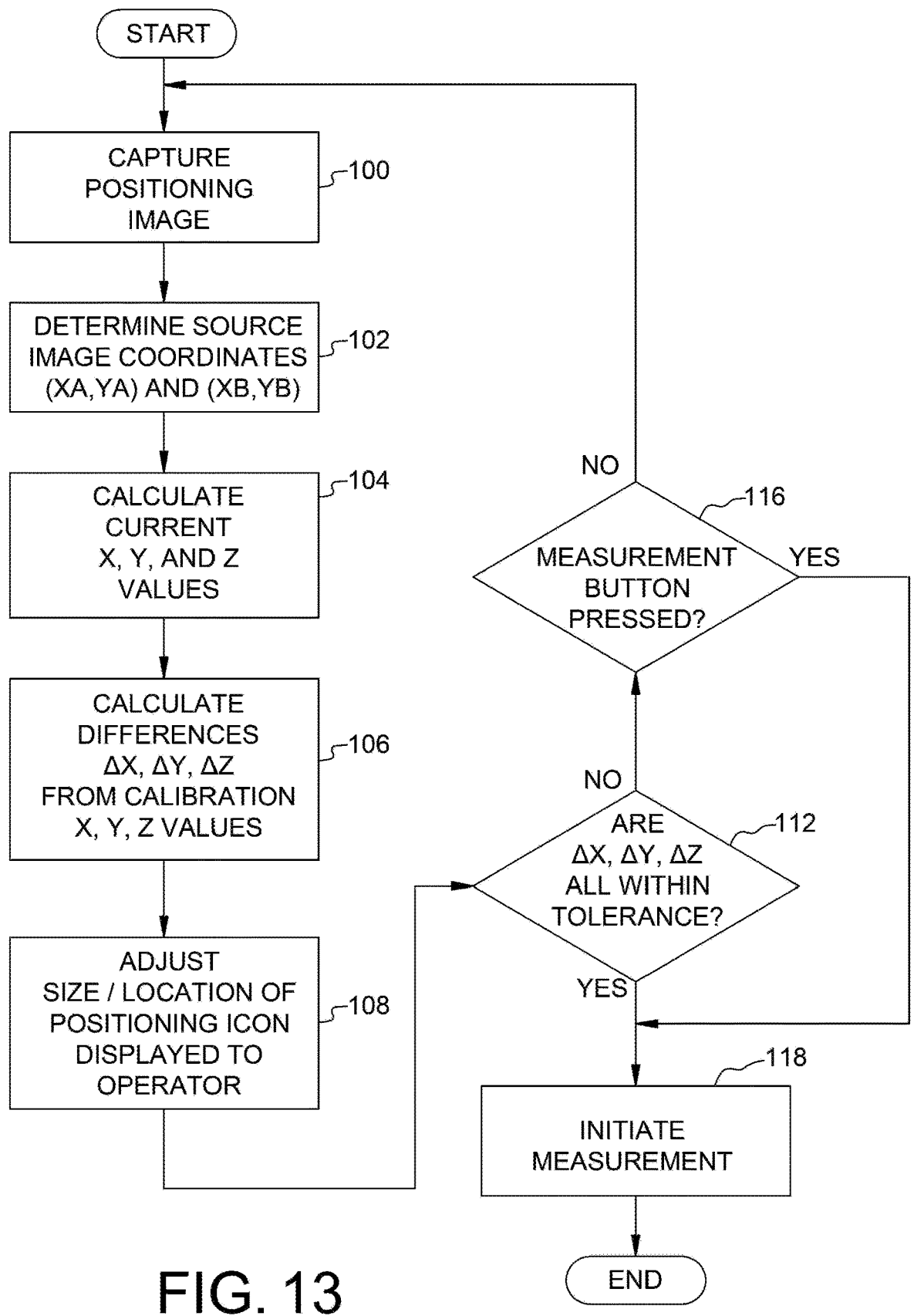

FIGS. 11A, 11B, and 11C show examples of positioning guidance images generated by the positioning system and displayed to an operator, wherein the positioning guidance images represent positioning images captured by the area detector of the positioning system together with a positioning target and a positioning icon;

FIG. 12 is a flow chart illustrating operation of the positioning system in a manual measurement mode of the ophthalmic instrument; and FIG. 13 is a flow chart illustrating operation of the positioning system in an automatic measurement mode of the ophthalmic instrument.

DETAILED DESCRIPTION OF THE INVENTION

FIGS. 1 through 5 show an ophthalmic instrument 10 for measuring an ophthalmic parameter of an eye in accordance with an embodiment of the present disclosure. In the figures, ophthalmic instrument 10 is embodied as a rebound tonometer for measuring IOP, however it is understood that ophthalmic instrument 10 may be embodied as a non-contact tonometer for measuring IOP, or may be embodied as another type of ophthalmic instrument for measuring a parameter of the eye other than IOP. Ophthalmic instrument 10 comprises a measurement axis 11. In the context of the illustrated rebound tonometer, measurement axis 11 is an axis along which a measurement probe 12 is propelled toward an eye of a test subject. In the context of a non-contact tonometer (not shown), measurement axis 11 is an axis of a fluid discharge tube through which a fluid pulse, e.g. an air puff, is directed at an eye of a test subject.

Ophthalmic instrument 10 may have a housing 14 defining a handle portion 16 and a measurement head 18 atop handle portion 16. A measurement button 20 may be provided on handle portion 16. When ophthalmic instrument 10 is in a manual operating mode, measurement button 20 is depressible by an operator to trigger a measurement by ophthalmic instrument 10. In the illustrated embodiment, measurement probe 12 has a magnetized shaft 12A coaxially received in a front coil 15 and a rear coil 16 provided in a tubular barrel 17A within measurement head 18 of housing 14. Front coil 15 may be energized momentarily to propel probe 12 toward the cornea by electromagnetic force. Rear coil 16 may serve as a sensing coil for sensing motion of probe 12, wherein current is induced in rear coil 16 to provide a detectable voltage signal representing velocity of the probe as a function of time. The voltage signal may be recorded and processed in a known manner to determine a measured IOP value.

Figure 1:
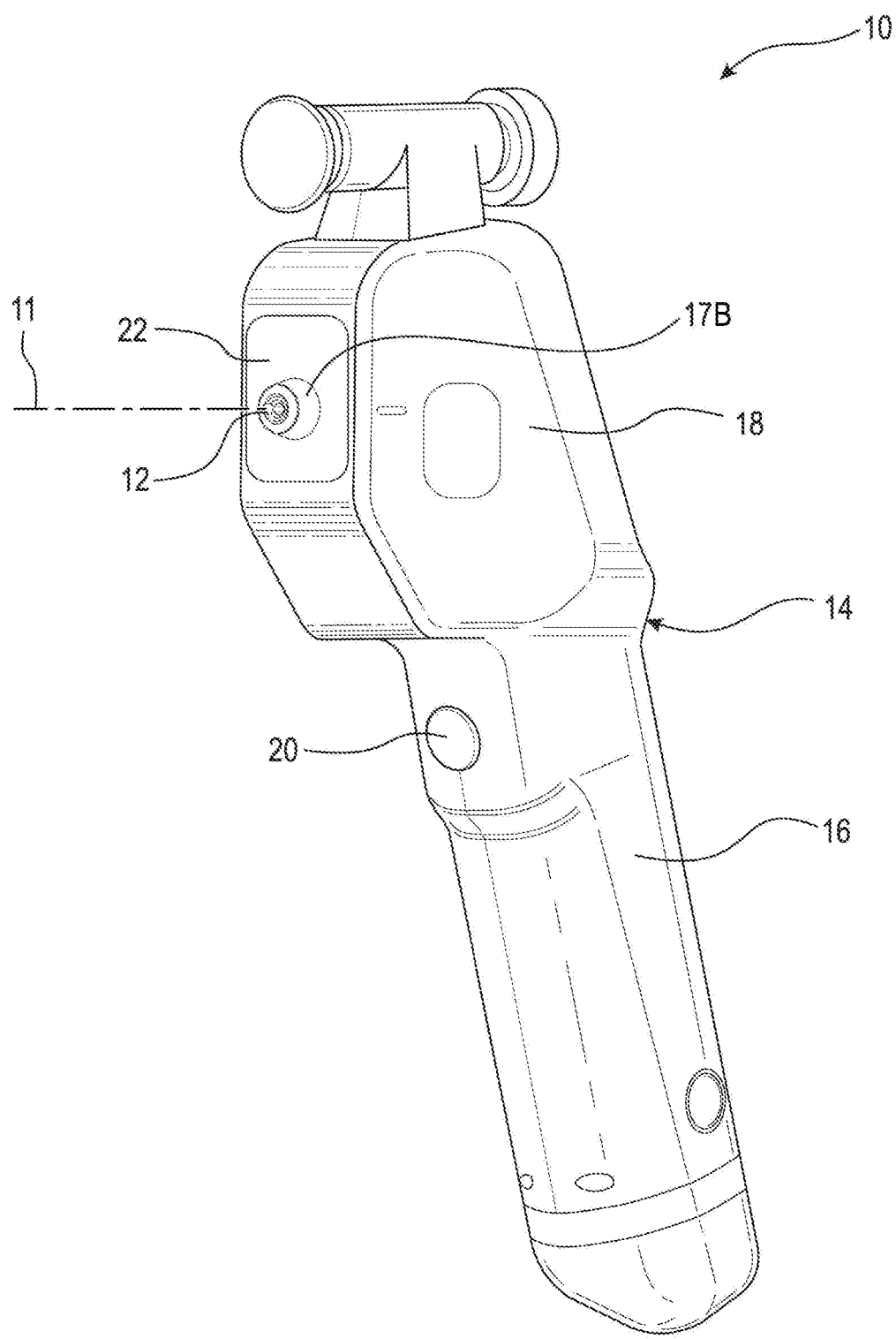
FIG. 1 is a perspective view of an ophthalmic instrument formed in accordance with an embodiment of the present disclosure.
Figure 2:
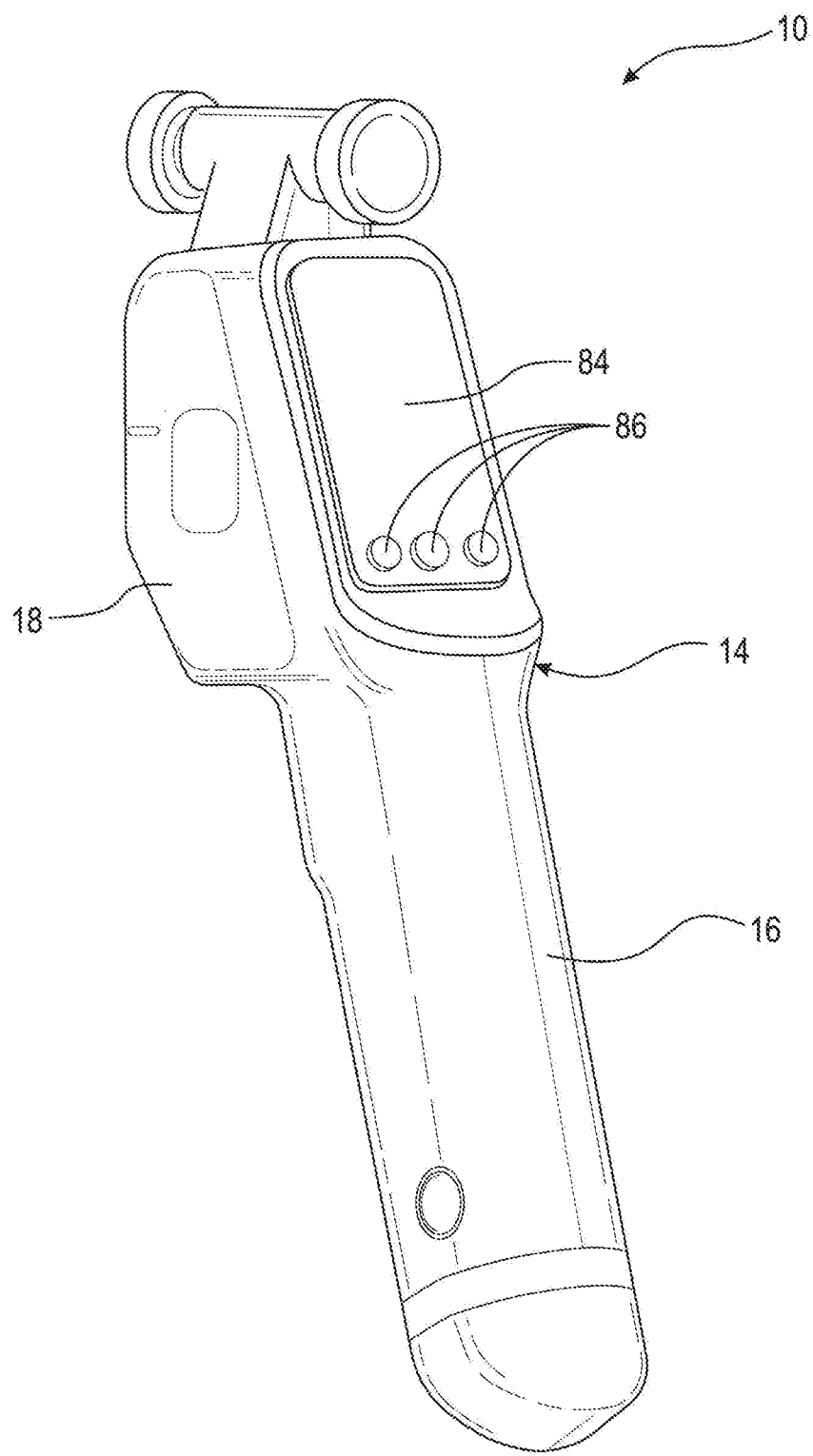
FIG. 2 is another perspective view of the ophthalmic instrument shown in FIG. 1.
Figure 3:
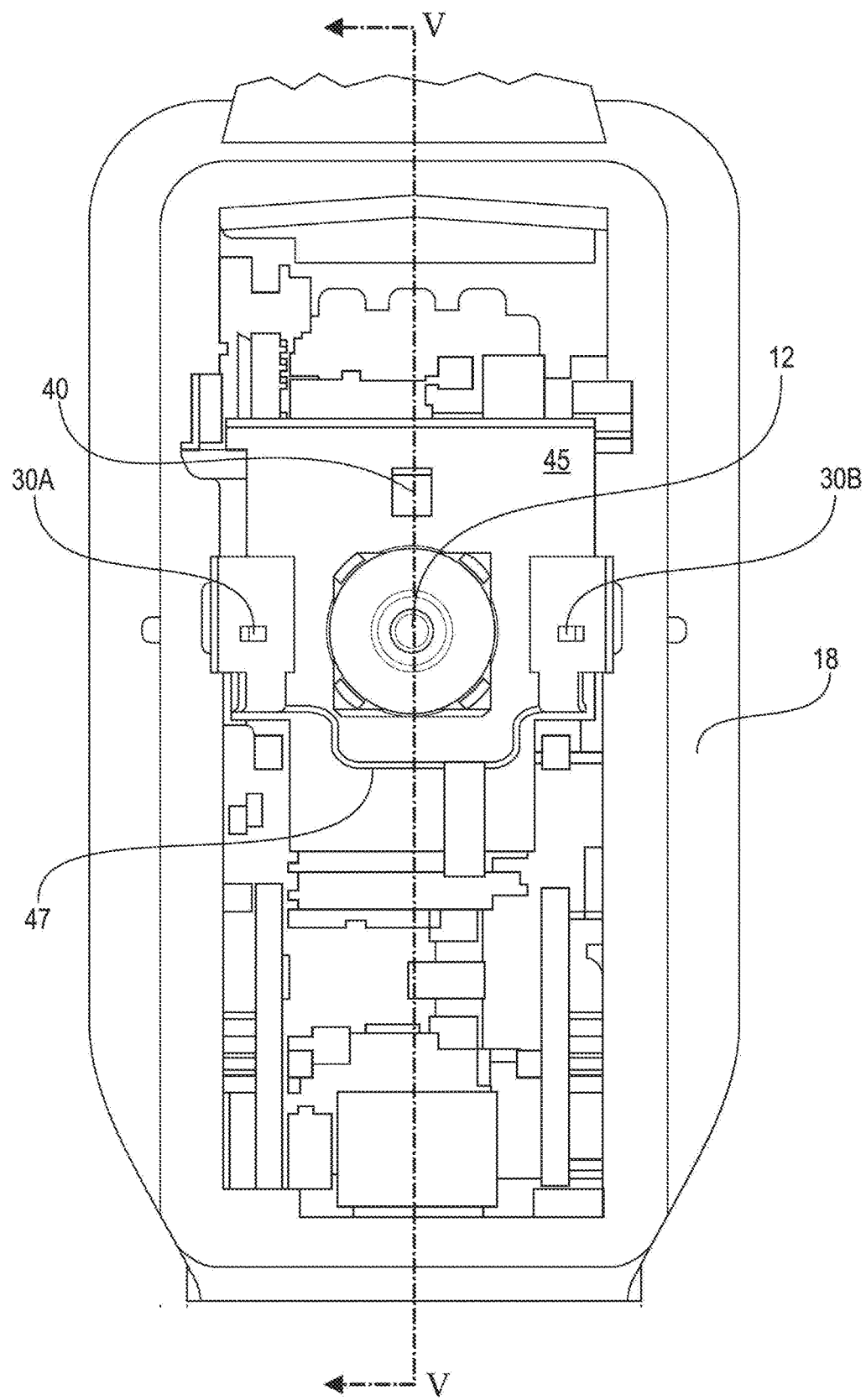
FIG. 3 is a front view of a measurement portion of the ophthalmic instrument, wherein cover parts are removed to show components of a positioning system of the ophthalmic instrument.
Figure 4:
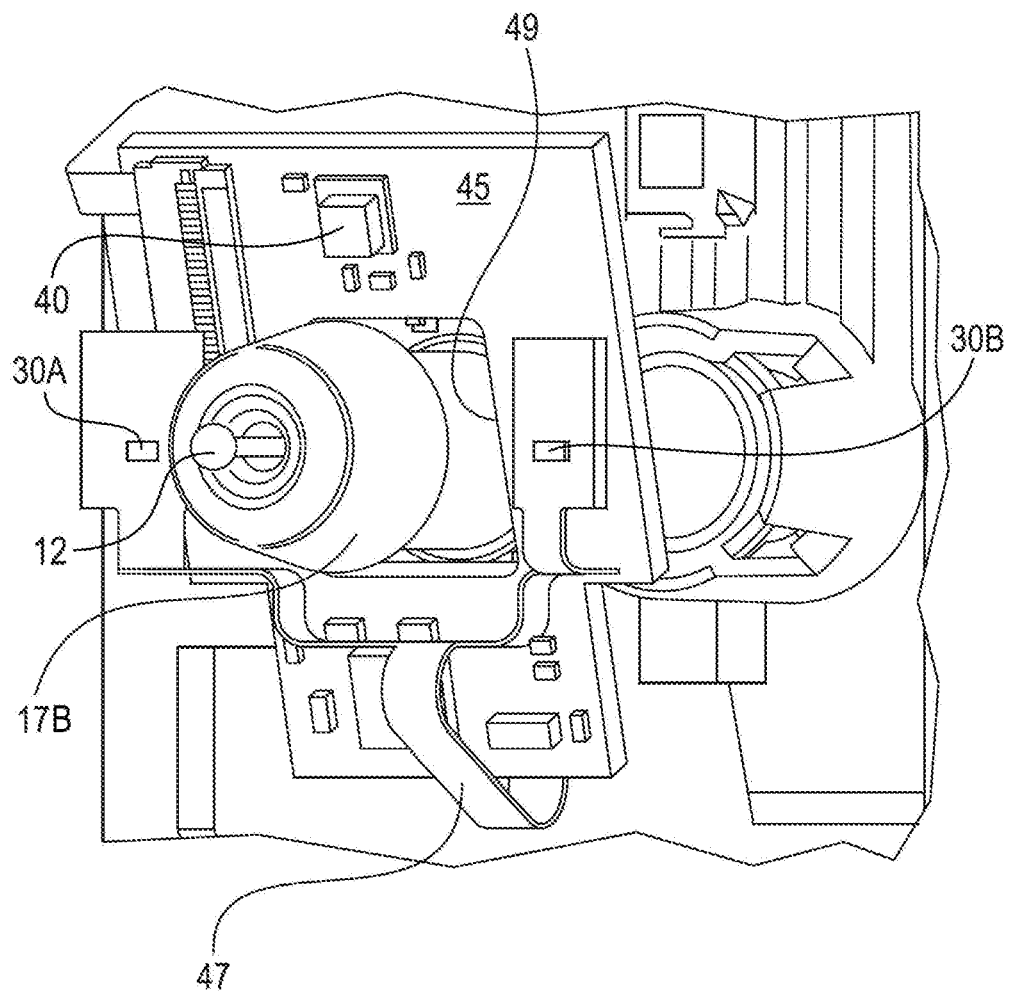
FIG. 4 is another view of the measurement portion of the ophthalmic instrument with cover parts removed to show components of the positioning system of the ophthalmic instrument.
Figure 5:
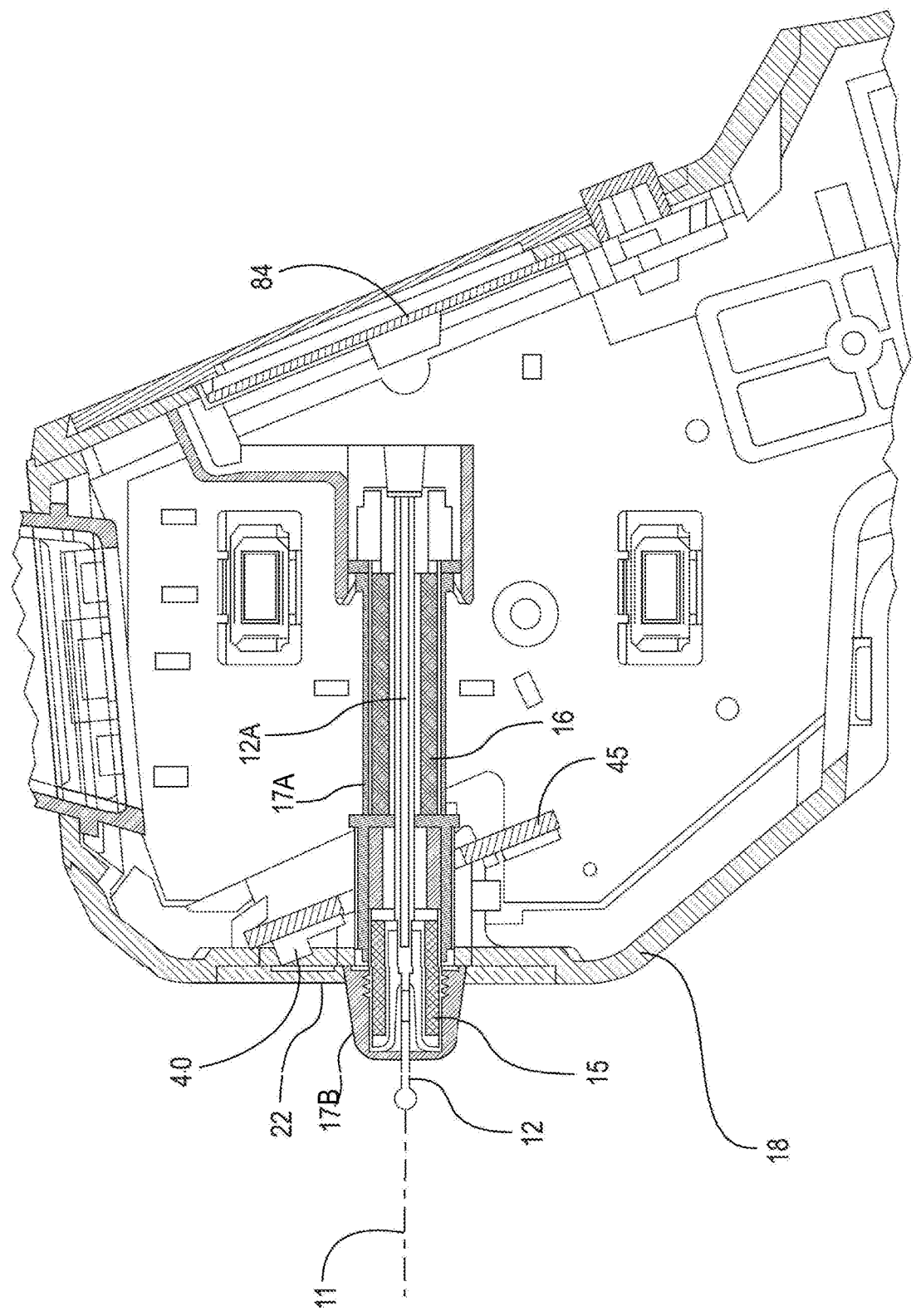
FIG. 5 is a cross-sectional view of the measurement portion of the ophthalmic instrument taken generally along the line V-V in FIG. 3.
Figure 6:
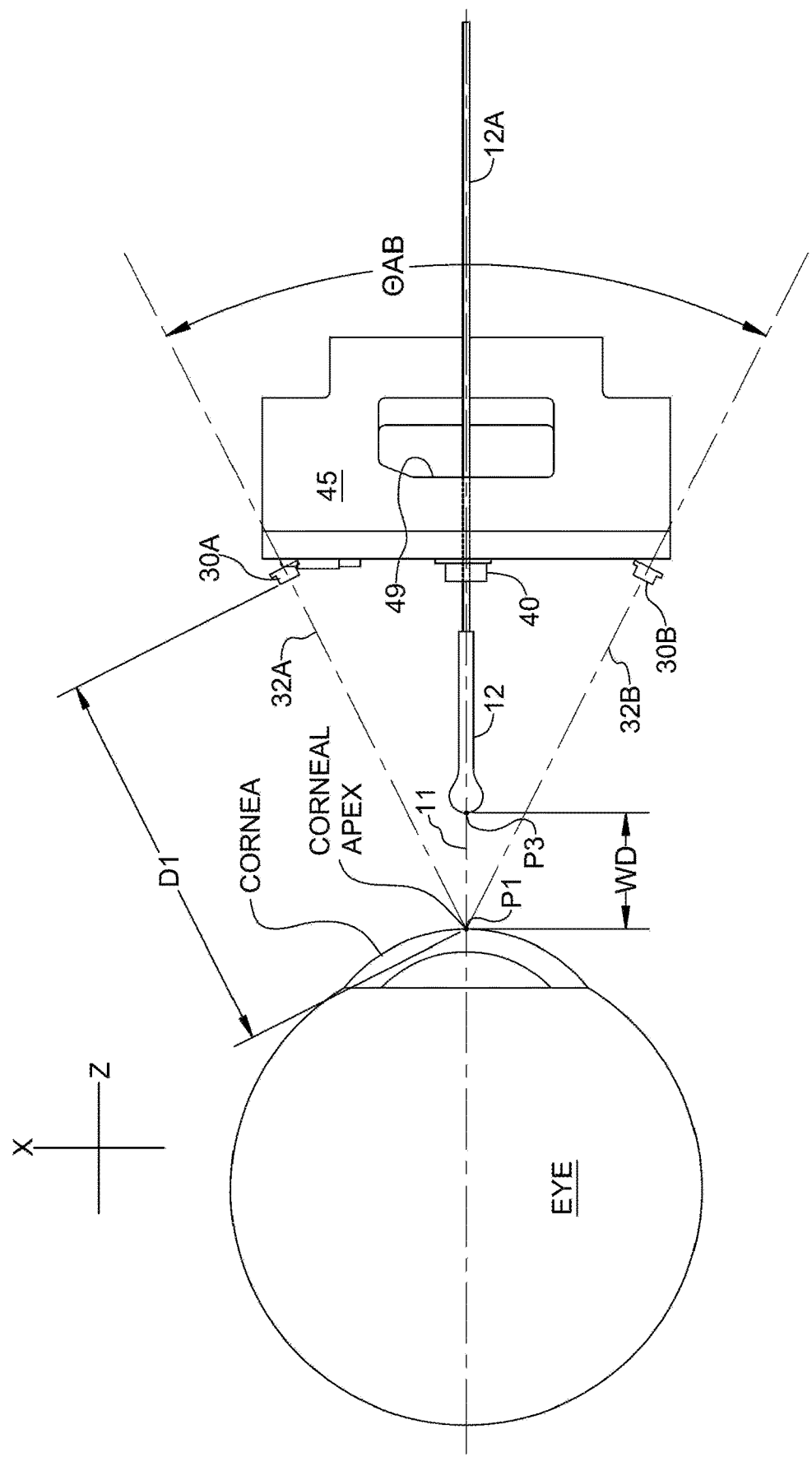
FIG. 6 is a schematic top view illustrating components of the positioning system in relation to an eye of a test subject.
Figure 7:
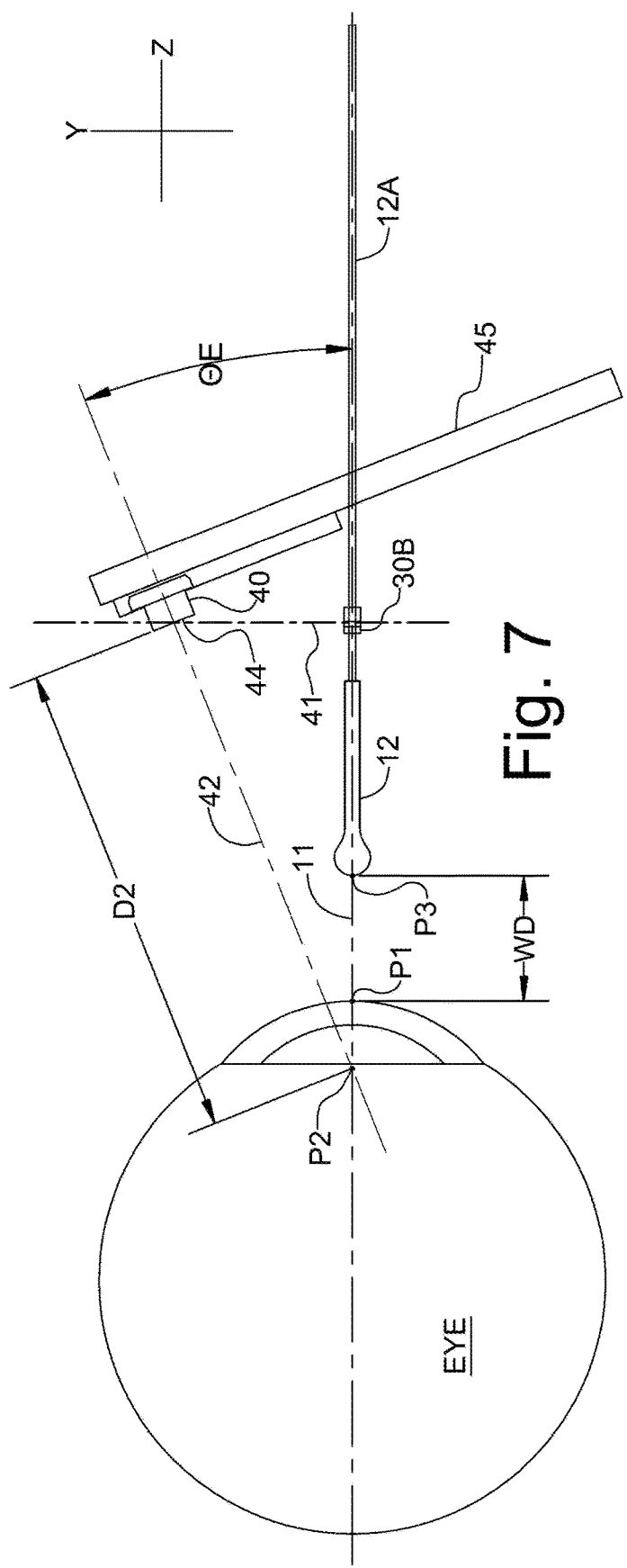
FIG. 7 is a schematic side view illustrating components of the positioning system in relation to an eye of a test subject.
Figure 8:
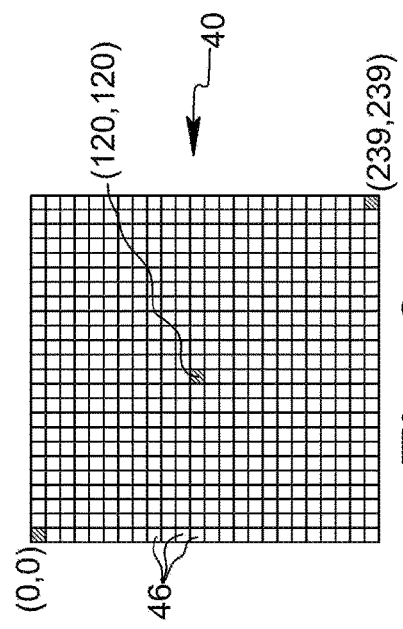
FIG. 8 is a schematic view of an area detector of the positioning system.

Reference is also made now to FIGS. 6 through 8. Ophthalmic instrument 10 comprises a positioning system including a first light source 30A spaced apart from measurement axis 11 and arranged to direct a first illumination beam along a first illumination axis 32A, and a second light source 30B spaced apart from measurement axis 11 and arranged to direct a second illumination beam along a second illumination axis 32B. The positioning system further includes an area detector 40 spaced apart from measurement axis 11 and from the first and second light sources 30A, 30B. Area detector 40 has an observation axis 42 extending normal to a detection plane 44 of the area detector in which a two-dimensional array of photosensitive pixels 46 is arranged. First illumination axis 32A, second illumination axis 32B, and observation axis 42 extend through a light-transmitting window 22 surrounding a probe base cap 17B at the front of measurement head 18. As will be described in greater detail below, area detector 40 is configured and arranged to continually capture positioning images of an eye when ophthalmic instrument 10 is positioned near the eye in preparation for a measurement.

By way of non-limiting example, each of first and second light sources 30A, 30B may be a light-emitting diode (LED) which emits red diffuse light. Use of red LEDs is advantageous because it allows the positioning system to distinguish between light associated with the positioning system and all other colors detected by area detector 40, and because it allows the test subject to use the red illuminated LEDs as fixation targets during a measurement. For example, the test subject may be instructed to fixate at a midpoint between the two red LEDs so that measurement axis 11 is normal to the corneal surface. Also by way of non-limiting example, area detector 40 may be a 640×480 color pixel image sensing array provided as part of a CameraCubeChip™ available from OmniVision of Santa Clara, Calif. under Part Number OVM7692-RYAA.

FIGS. 3 through 7 illustrate one possible implementation of the positioning system in which area detector 40 is mounted on a circuit board 45, and light sources 30A, 30B are mounted on respective branches of a bifurcated flexible connector 47 extending from circuit board 45. As best seen in FIG. 7, circuit board 45 may be inclined with respect to measurement axis 11 such that observation axis 42 of area detector 40 forms an elevation angle $\ominus E$ with measurement axis 11. Circuit board 45 may include an opening 49 through which barrel 17A may extend. In the depicted implementation, first illumination axis 32A and second illumination axis 32B are coplanar with measurement axis 11 in a horizontal plane and form an angle $\ominus AB$ which is bisected by measurement axis 11. According to the illustrated implementation, observation axis 42 may be coplanar with measurement axis 11 in a vertical plane. First illumination axis 32A and second illumination axis 32B may converge at a first point P1 along measurement axis 11 within a field of view of area detector 40, and observation axis 42 may intersect measurement axis 11 at a second point P2 along measurement axis 11 spaced from first point P1. Ophthalmic instrument 10 may further comprise a working distance reference point P3 on measurement axis 11, wherein a working distance WD of instrument 10 relative to the eye is defined as the distance between reference point P3 and the corneal surface of the eye. For example, where ophthalmic instrument 10 is a rebound tonometer, working distance reference point P3 may be a point at a front tip of measurement probe 12, and where ophthalmic instrument 10 is a non-contact tonometer, working distance reference point P3 may be a point at a front tip of a fluid discharge tube of the tonometer. In the illustrated implementation, a distance between reference point P3 and second point P2 is greater than a distance between reference point P3 and first point P1. As best understood from FIGS. 6 and 7, first light source 30A, second light source 30B, and area detector 40 may be arranged such that they are intersected by a plane 41 which is normal to measurement axis 11.

With regard to the illustrated implementation, the following dimensions may be used in practice, however these dimensions are provided merely as examples and with the understanding that other dimensions may be used in practice: working distance WD=6.00 mm; illumination axis angle $\ominus AB=53.6°$; observation axis elevation angle $\ominus E=21.8°$; illumination distance D1=20.012 mm (for both light sources 30A and 30B); and observation distance D2=23.07 mm.

Figure 9:
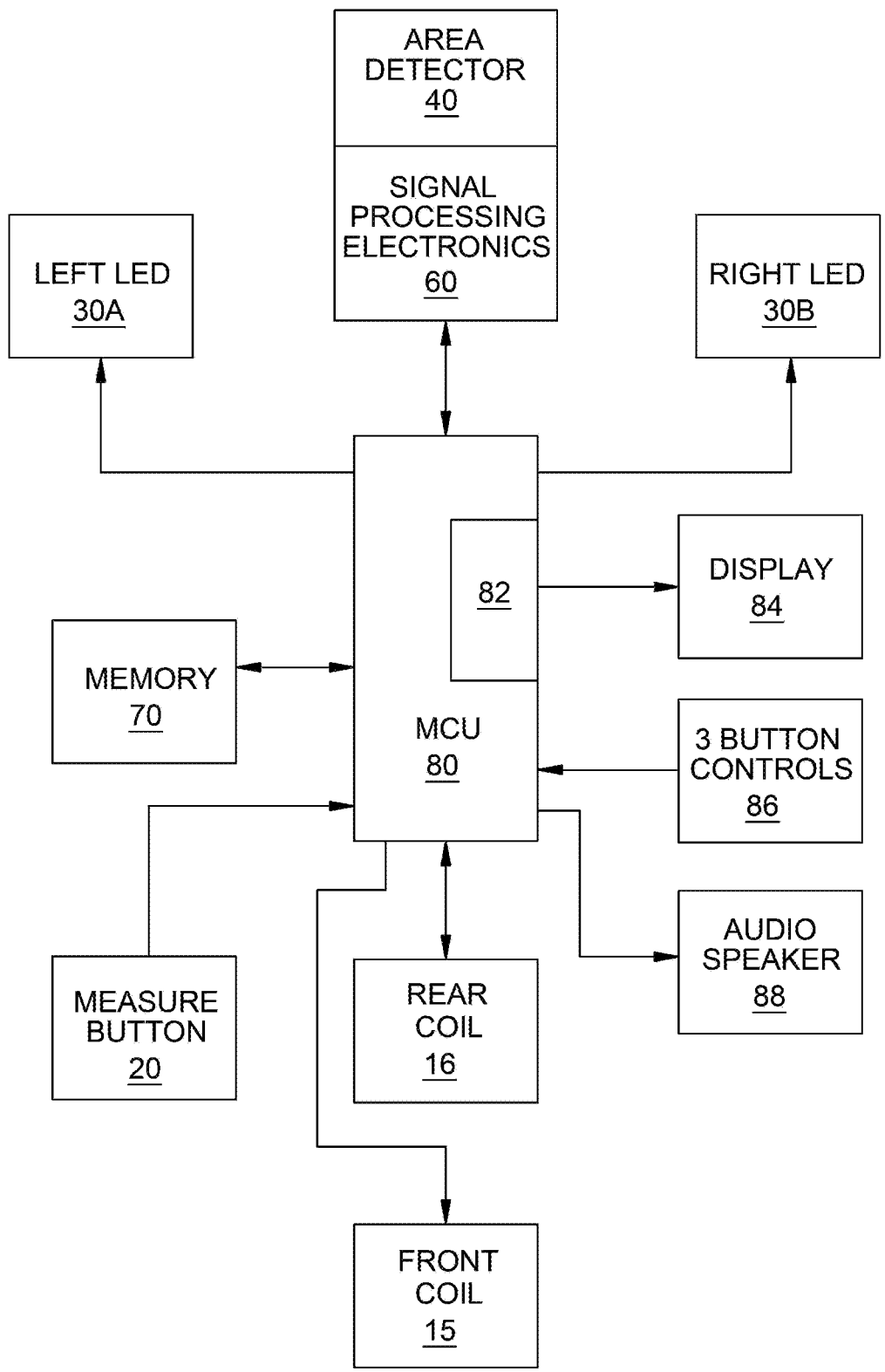
FIG. 9 is a schematic electronic block diagram of the ophthalmic instrument.

FIG. 9 is a schematic electronic block diagram of ophthalmic instrument 10. Ophthalmic instrument 10 comprises signal processing electronics 60 connected to area detector 40 for receiving the plurality of pixel signals and converting the plurality of pixel signals to a digital positioning image. For example, signal processing electronics 60 may be embodied by on-board signal processing electronics provided as part of the aforementioned CameraCubeChip™, which includes an analog-to-digital converter, a digital signal processor and formatter, and an image output interface.

Ophthalmic instrument 10 also comprises a memory 70 which stores positioning calibration information. For example, memory 70 may be embodied as a nonvolatile memory which retains stored information when power to ophthalmic instrument 10 is shut off. Memory 70 may be a ferroelectric random access memory (F-RAM) module or another type of memory. An example of a suitable F-RAM module is available from Cypress Semiconductor Corporation under Part Number FM24V10GTR.

Ophthalmic instrument 10 comprises a microcontroller 80 programmed by software instructions stored in memory to control various operating functions of ophthalmic instrument 10. By way of non-limiting example, microcontroller 80 may be embodied as a microcontroller available from STMicroelectronics under Part Number STM32L4R9AII6, which has an ARM® CORTEX®-M4 core as the central processing unit (CPU) and embedded Flash memory. Alternatively, microcontroller 80 may be embodied as another type of controller configured to control operating functions of ophthalmic instrument 10.

Ophthalmic instrument 10 further comprises an image evaluation module 82 configured by stored software instructions to evaluate the digital positioning images which are output from signal processing electronics 60 with reference to the positioning calibration information stored in memory 70, and to compute a position difference representing a difference between a current three-dimensional position of ophthalmic instrument 10 relative to the eye and an ideal three-dimensional position of the ophthalmic instrument 10 relative to the eye. As illustrated in FIG. 9, image evaluation module 82 may be incorporated in microcontroller 80. Alternatively, image evaluation module 82 may be embodied by a separate computational circuit module connected to microcontroller 80.

Ophthalmic instrument 10 also comprises a display 84 connected to microcontroller 80 for presenting information to an operator. For example, display 84 may be used to display measurement results and other measurement data to an operator. Display 84 may also be used to present positioning guidance images to an operator to help guide the operator in positioning ophthalmic instrument 10 relative to an eye of a test subject for a measurement as described in greater detail below. By way of non-limiting example, display 84 may be a liquid crystal display (LCD).

Ophthalmic instrument 10 may further comprise menu navigation/selection buttons 86 connected to microcontroller 80 and enabling an operator to set operating parameters of ophthalmic instrument 10 in conjunction with operating system menus displayed on display 84. Ophthalmic instrument 10 may also comprise an audio speaker 88 connected to microcontroller 80.

In an aspect of the present disclosure, first light source 30A and second light source 30B may fit within a lateral distance LD which is less than or equal to 25 mm (about one inch). This lateral distance limitation is critical in several important ways. First, it enables the lateral width of measurement head 18 to be limited to approximately 37 mm (some lateral space on both sides of light sources 30A, 30B is needed for housing structure and hardware for mounting internal components in measurement head 18). This is important because it helps prevent the side of measurement head 18 from contacting the nose of the test subject when measurement axis 11 is positioned in front of an eye for taking a measurement. As shown in the drawing figures, measurement axis 11 may be positioned midway between the lateral sides of measurement head 18, such that the distance from each lateral side of measurement head 18 to measurement axis 11 is no greater than approximately 19 mm. The lateral distance from the center of each pupil to the corresponding near side of the nose is slightly less than half the interpupillary distance. Since the interpupillary distance of an adult human is typically in a range of about 54 mm-74 mm, the pupil-to-nose distance is usually in a range of about 23 mm-32 mm. Consequently, by fitting light sources 30A, 30B within a lateral distance LD of 25 mm, thereby limiting the lateral distance from measurement axis 11 to each side surface of measurement head to about 19 mm, some clearance is maintained between the side of measurement head 18 and the bridge of the test subject's nose during measurement.

A second way limitation of lateral distance LD to 25 mm is critical is that it provides the operator with a direct view of the eye being tested in addition to a direct view of display 84. As may be understood, the length of measurement head 18 front-to-rear is primarily dictated by structure for propelling probe 12 (or, in the case of a non-contact tonometer, structure for generating and discharging an air pulse). Applicant has found that in order to provide an adult human operator having an interpupillary distance in a range of about 54 mm-74 mm an unimpeded direct view of the eye during a measurement, the lateral width of measurement head 18 must be limited to approximately 37 mm. Consequently, given the need for housing structure and other hardware for mounting internal measurement components in measurement head 18, light sources 30A, 30B must be kept within the lateral distance LD of 25 mm to ensure a direct view of the eye by the operator during a measurement.

As described above, area detector 40 captures positioning images of an eye when ophthalmic instrument 10 is positioned near the eye in preparation for a measurement, and the captured positioning images are converted from analog to digital format by signal processing electronics 60. The digital positioning images are evaluated by image evaluation module 82 to provide information indicating the positioning status of ophthalmic instrument 10 relative to the eye in three dimensions X, Y, and Z. To enable image evaluation, ophthalmic instrument 10 is calibrated using a false "calibration eye," for example a false eye made of glass, to capture at least one calibration image from which positioning calibration information is determined and stored in memory 70. The calibration eye maybe, for example, a glass spherical ball having a radius of eight millimeters, which is approximately the average radius of curvature of an anterior surface of a human cornea. The calibration image is captured when ophthalmic instrument 10 is at an ideal three-dimensional position relative to the calibration eye for carrying out a measurement. For example, the ideal three-dimensional position may correspond to a condition in which measurement axis 11 intersects the corneal apex and is substantially perpendicular to the local corneal surface at the corneal apex, and the tip P3 of probe 12 is at a predetermined working distance WD away from the corneal surface. In a current embodiment, the predetermined working distance WD may be six millimeters, however the predetermined working distance WD may be another value. Where ophthalmic instrument 10 is a rebound tonometer, calibration may be carried out using a calibration tool which incorporates the calibration eye and mounts directly in ophthalmic instrument 10 along measurement axis 11 in place of a probe 12. For example, the calibration eye may be mounted at an end of a shaft which is similar to probe shaft 12A whereby the calibration tool shaft may be releasably and coaxially retained in front coil 15 and rear coil 16 of ophthalmic instrument 10. The calibration tool may be configured so that when the calibration tool is mounted in ophthalmic instrument 10, the calibration eye is located such that an apex of the calibration eye is intersected by measurement axis 11 at a Z-axis position corresponding to the predetermined working distance WD from the front tip of a probe 12 if a probe 12 were mounted in ophthalmic instrument 10 instead of the calibration tool. Where ophthalmic instrument 10 is a non-contact tonometer, the calibration tool may have a mounting shaft sized for slidable receipt within the axial passage of the fluid pulse (e.g. air puff) discharge tube to align the calibration eye on measurement axis 11 at an ideal Z-axis working distance from an exit end of the discharge tube for purposes of calibration.

Figure 10:
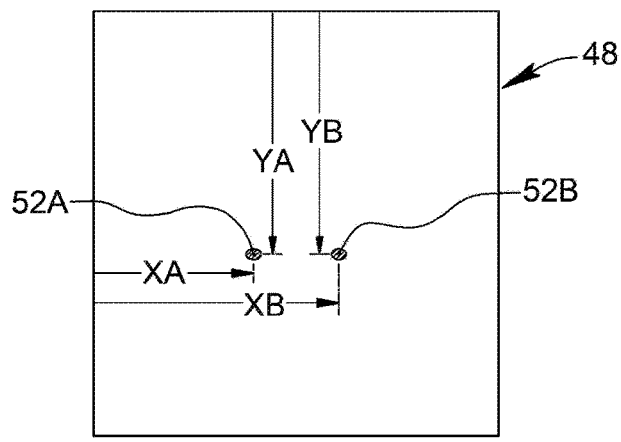
FIG. 10 is an example of a calibration image captured by the area detector of the positioning system.

FIG. 10 shows an example of a calibration image 48 captured by area detector 40 when ophthalmic instrument 10 is at the predetermined ideal three-dimensional measurement position relative to a calibration eye, and digitized by signal processing electronics 60. Calibration image 48 represents a reflected-light image of a facing surface region of the calibration eye when first light source 30A and second light source 30B are illuminated. Consequently, calibration image 48 includes a first source image 52A corresponding to first light source 30A and a second source image 52B corresponding to second light source 30B. Image evaluation module 82 may be programmed to evaluate calibration image 48 to determine location coordinates XA, YA of first source image 52A and location coordinates XB, YB of second source image 52B, wherein the location coordinates represent a location of the corresponding source image in the two-dimensional sensing surface of area detector 40. For example, the coordinate values may be based on pixel values counted relative to an origin corner of the sensing surface of area detector 40, as illustrated in FIG. 8. Evaluation of calibration image 48 to determine the locations of source images 52A, 52B may involve finding the pixel groups registering the highest intensity for a specific color corresponding to the color of light sources 30A, 30B. For example, where area detector 40 is a color Red-Green-Blue (RGB) sensor, and light sources 30A, 30B are red LEDs, the red, green, and blue pixel color separation may be analyzed to differentiate the red LED reflections defining source images 52A, 52B from the rest of calibration image 48. Exclusion criteria may be applied to the location, size, intensity, and/or separation of source images 52A, 52B to prevent false location detection. The respective centroids of source images 52A, 52B may be calculated to determine the corresponding two-dimensional locations (XA, YA) and (XB, YB) of source images 52A, 52B.

The two-dimensional locations (XA, YA) and (XB, YB) of source images 52A, 52B in calibration image 48 may be stored directly in memory 70 and/or used to calculate a three-dimensional calibration position coordinate ($X_{CAL}$, $Y_{CAL}$, $Z_{CAL}$) stored in memory 70. For example, the three-dimensional calibration position coordinate ($X_{CAL}$, $Y_{CAL}$, $Z_{CAL}$) may be calculated as follows. $X_{CAL}$, which corresponds to an ideal horizontal left-right position of ophthalmic instrument 10 relative to an eye, may be calculated as the average X location of the two source images 52A, 52B in calibration image 48:

$$X_{CAL} = (XA + XB)/2$$

$Y_{CAL}$, which corresponds to an ideal vertical up-down position of ophthalmic instrument 10 relative to an eye, may be calculated as the average Y location of the two source images 52A, 52B in calibration image 48:

$$Y_{CAL} = (YA + YB)/2$$

$Z_{CAL}$, which corresponds to an ideal working distance position of ophthalmic instrument 10 along measurement axis 11 relative to an eye, may be calculated as the horizontal spacing between the two source images 52A, 52B in calibration image 48:

$$Z_{CAL} = XB - XA$$

As may be understood, the horizontal spacing between source images 52A, 52B is inversely proportional to the working distance. In other words, as the working distance of ophthalmic instrument 10 from the eye is decreased, the horizontal spacing between source images 52A, 52B will increase, and as the working distance of ophthalmic instrument 10 from the eye is increased, the horizontal spacing between source images 52A, 52B will decrease.

The two-dimensional locations (XA, YA) and (XB, YB) of source images 52A, 52B, and the three-dimensional calibration position coordinate ($X_{CAL}$, $Y_{CAL}$, $Z_{CAL}$), may individually and/or collectively be considered "positioning calibration information." The positioning calibration information determined through calibration of ophthalmic instrument 10 as described above may be stored in memory 70 for later use during a normal (i.e. non-calibration) measurement procedure to determine when ophthalmic instrument 10 is near enough to the ideal three-dimensional measurement position to allow a measurement to be initiated.

FIGS. 11A, 11B, and 11C illustrate examples of positioning images 50 captured by area detector 40 during a normal measurement procedure, as displayed to an operator on display 84 together with a superimposed positioning target 90 and a positioning icon 92. As with calibration image 48, area detector 40 generates a plurality of pixel signals collectively representing each positioning image, and the pixel signals are digitized by signal processing electronics 60 to provide a digital positioning image 50. In the examples shown in FIGS. 11A, 11B, and 11C, a portion of the eye to be measured, including the pupil of the eye, is within a field of view of area detector 40 and is visible in positioning image 50. Similar to calibration image 48, each positioning image 50 may include a first source image 52A corresponding to first light source 30A and a second source image 52B corresponding to second light source 30B.

Positioning target 90 represents the ideal three-dimensional position of ophthalmic instrument 10 relative to the eye. Positioning target 90 may be centered at an XY location on display 84 corresponding to the $X_{CAL}$ and $Y_{CAL}$ values of the three-dimensional calibration position coordinate ($X_{CAL}$, $Y_{CAL}$, $Z_{CAL}$), and a size of a fitting portion 91 of positioning icon 90 may be scaled based on the $Z_{CAL}$ value of the three-dimensional calibration coordinate ($X_{CAL}$, $Y_{CAL}$, $Z_{CAL}$). For example, positioning target 90 may include a continuous or segmented circular ring centered and scaled based on the three-dimensional calibration coordinate ($X_{CAL}$, $Y_{CAL}$, $Z_{CAL}$). Other shapes and forms may be used for positioning target 90, for example a cross or a square.

Positioning icon 92 represents the current three-dimensional position of ophthalmic instrument 10 relative to the eye. Image evaluation module 82 may be configured to generate positioning icon 92 by calculating a current three-dimensional position coordinate (X, Y, Z) based on the two-dimensional locations (XA, YA) and (XB, YB) of source images 52A, 52B in positioning image 50, rendering positioning icon 92 so that the positioning icon is centered at an XY location on display 84 corresponding to the X and Y values of the current three-dimensional position coordinate (X, Y, Z), and scaling a size of positioning icon 92 based on the Z value of the current three-dimensional position coordinate (X, Y, Z). The current three-dimensional position coordinate (X, Y, Z) may be calculated from positioning image 50 the same way the three-dimensional calibration position coordinate ($X_{CAL}$, $Y_{CAL}$, $Z_{CAL}$) is calculated from calibration image 48, as described above. In the illustrated embodiment, positioning icon 92 is in the form of a circular ring, however other shapes and forms may be used, for example a cross or a square.

Image evaluation module 82 may be configured to output digital positioning image 50, positioning target 90, and positioning icon 92 to display 84, wherein digital positioning image 50, positioning target 90, and positioning icon 92 are superimposed to provide a positioning guidance image displayed on display 84 for guiding an operator in positioning ophthalmic instrument 10 relative to the eye to take a measurement. The center of positioning icon 92 may be located in the displayed guidance image at the XY location indicated by the current three-dimensional position coordinate (X, Y, Z). For example, in FIG. 11A, the center of positioning icon 92 is located above and to the right of the center of positioning target 90, which illustrates a situation in which measurement axis 11 of instrument 10 is below and to the left of the corneal apex, and instrument 10 must be moved upward and to the right (i.e., the operator is guided to move instrument 10 in a direction from positioning target 90 toward positioning icon 92). As another example, in FIG. 11B, the center of positioning icon 92 is located just below and to the left of the center of positioning target 90, which illustrates a situation in which measurement axis 11 of instrument 10 is just above and to the right of the corneal apex, and instrument 10 must be moved slightly downward and to the left. In the example of FIG. 11C, the center of positioning icon 92 and the center of positioning target 90 are approximately at the same location, indicating that instrument 10 is at the ideal XY alignment position wherein measurement axis 11 intersects the corneal apex.

Positioning icon 92 may be scaled based on the Z value of the current three-dimensional position coordinate (X, Y, Z) such that a size of the positioning icon is inversely proportional to a working distance of ophthalmic instrument 10 from the eye along measurement axis 11 (i.e., as ophthalmic instrument 10 is moved closer to the eye along measurement axis 11, positioning icon 92 grows larger in the displayed positioning guidance image). When positioning icon 92 corresponds in size to fitting portion 91 of positioning target 90, as shown for example in FIG. 11C, then ophthalmic instrument 10 is at the predetermined desired working distance WD away from the cornea for taking a measurement. As may be understood, in FIG. 11A, instrument 10 is too far away from the eye for measurement, and in FIG. 11B, instrument 10 is too close to the eye for measurement.

As mentioned above, image evaluation module 82 may be configured by stored software instructions to compute a position difference representing a difference between the current three-dimensional position of ophthalmic instrument 10 represented by coordinate (X, Y, Z) and the ideal three-dimensional position of ophthalmic instrument 10 represented by coordinate calibration coordinate ($X_{CAL}$, $Y_{CAL}$, $Z_{CAL}$). For example, a position difference (ΔX, ΔY, ΔZ) may be calculated as follows:

$$\Delta X = X - X_{CAL},$$

$$\Delta Z = Z - Z_{CAL}, \text{ and}$$

$$\Delta Y = Y - Y_{CAL} - \Delta Z.$$

In the calculation of ΔY, subtracting ΔZ compensates for the change in camera angle (i.e. the change in the elevation angle ΘE of observation axis 42) as the Z distance from the eye changes. Proper positioning of instrument 10 relative to the eye for measurement purposes may be judged by whether or not the computed position difference is within a predetermined positioning tolerance for measurement purposes. For example, to be within the predetermined positioning tolerance, the current X, Y pixel position of instrument 10 must be within a predetermined radius of the pixel location $X_{CAL}$, $Y_{CAL}$, and an absolute value of ΔZ must be less than or equal to a predetermined Z axis tolerance expressed in pixels. In spatial coordinates, it has been found that measurement axis 11 is preferably within a radius of 1 mm from the corneal apex in the X and Y positioning directions, and within ±1.5 mm of the ideal working distance in the Z positioning direction, however other values may be used. Instead of requiring the current X, Y pixel position of instrument 10 to be within a predetermined radius of the pixel location $X_{CAL}$, $Y_{CAL}$, a bounding box centered around pixel location $X_{CAL}$, $Y_{CAL}$ may be defined whereby each of ΔX and ΔY must be within its own respective tolerance.

An appearance attribute of positioning icon 92 may be dependent upon whether or not the computed position difference is within the predetermined positioning tolerance for measurement purposes. In this way, the positioning guidance image displayed to the operator may indicate to the operator whether or not acceptable positioning is achieved. The appearance attribute may be the color of positioning icon 92. Accordingly, if the computed position difference is not within the predetermined positioning tolerance (i.e. instrument 10 is not properly positioned in three dimensions for a measurement), then positioning icon 92 may be generated to have a predetermined first color, for example yellow. This may be considered a "NO GO" appearance of positioning icon 92. If the computed position difference is within the predetermined positioning tolerance (i.e. instrument 10 is properly positioned in three dimensions for a measurement), then positioning icon 92 may be generated to have a predetermined second color different from the first color, for example green. This may be considered a "GO" appearance of positioning icon 92. The appearance attribute may be an attribute other than color, such as an On/Off blink rate applied to positioning icon 92. More than one appearance attribute of positioning icon 92 may be controlled depending on whether or not the computed position difference is within the predetermined positioning tolerance.

Reference is now made to FIGS. 12 and 13 to describe manual and automatic measurement modes of ophthalmic instrument 10, respectively. A chosen measurement mode, manual or automatic, may be selected using menu navigation/selection buttons 86.

FIG. 12 illustrates a manual measurement mode of instrument 10. In step 100, a positioning image 50 is captured by area detector 40. In steps 102, 104, 106, and 108, the source image coordinates (XA, YA) and (XB, YB) are determined, the current positioning coordinate (X, Y, Z) and position difference (ΔX, ΔY, ΔZ) are calculated, and the size (scale) and location of the displayed positioning icon 92 are adjusted. These steps are described in detail above. A decision block 112 then determines whether or not the computed position difference is within a predetermined positioning tolerance for measurement purposes. If not, an appearance attribute of positioning icon 92 is set to or maintained in a "NO GO" appearance in step 110, but if so, an appearance attribute of positioning icon 92 is set to a "GO" appearance in step 114. These steps are also described in greater detail above. From step 110 or step 114, flow proceeds to decision block 116. Decision block 116 waits for a signal generated in response to the operator pressing measurement button 20, and measurement is initiated in block 118 when the button is pressed. If measurement button 20 is not pressed within a predetermined time period, then flow returns to step 100. Thus, if the operator fails to promptly press measurement button 20, then positioning must be reevaluated to account for any intervening movement of instrument 10 relative to the eye.

The automatic measurement mode illustrated in FIG. 13 is similar to the manual mode with regard to steps 100, 102, 104, 106, 108, and 112. However, if decision block 112 determines that the computed position difference is within the predetermined positioning tolerance for measurement purposes, then flow branches directly to step 118 and a measurement is automatically initiated (i.e. the operator does not have to press measurement button 20 to initiate the measurement). For automatic measurement mode, image evaluation module 82 may be connected to microcontroller 80 and configured to send a position confirmation signal to the microcontroller when the computed position difference is within the predetermined positioning tolerance, and microcontroller 80 may automatically initiate the measurement in response to the position confirmation signal. If decision block 112 determines that the computed position difference is not within the predetermined positioning tolerance for measurement purposes, then flow proceeds to decision block 116 to wait for the measurement button pressing signal, and measurement is initiated in block 118 when the button 20 is pressed. If measurement button 20 is not pressed within a predetermined time period, then flow returns to step 100.

The positioning system of the present disclosure provides several practical benefits for a hand-held ophthalmic instrument. By keeping the measurement head 18 of the instrument as narrow as possible, the amount of parallax error for operators using the instrument in manual mode is reduced. By limiting the lateral distance occupied by first and second light sources 30A, 30B, the size and pixel count of area detector 40 may be reduced, which improves processing speed to avoid lag between the displayed positioning guidance image and reality. Moreover, in cases where the cornea of the eye being measured is an asymmetrical cornea, the effects of corneal asymmetry are amplified if the first and second light sources 30A, 30B are spaced too widely. This allows the instrument to obtain measurements at different areas of the cornea (like the limbus) without impacting positioning system error as much as a positioning system having wider-spaced light sources. In summary, the undesirable influence of corneal curvature is reduced by placing the first and second light sources 30A, 30B and area detector 40 in a smaller area.

While the present disclosure describes exemplary embodiments, the detailed description is not intended to limit the scope of the appended claims to the particular embodiments set forth. The claims are intended to cover such alternatives, modifications and equivalents of the described embodiments as may be included within the scope of the claims.

What is claimed is:

1. An ophthalmic instrument for measuring an ophthalmic parameter of an eye, the ophthalmic instrument comprising:
    a measurement axis;
    a first light source spaced apart from the measurement axis, the first light source directing a first illumination beam along a first illumination axis;
    a second light source spaced apart from the measurement axis and the first light source, the second light source directing a second illumination beam along a second illumination axis;
    an area detector spaced apart from the measurement axis and from the first and second light sources, the area detector having an observation axis, wherein the area detector captures a positioning image of the eye when the ophthalmic instrument is positioned near the eye in preparation for a measurement, the positioning image including a first source image corresponding to the first light source and a second source image corresponding to the second light source, and wherein the area detector generates a plurality of pixel signals collectively representing the positioning image;
    signal processing electronics connected to the area detector for receiving the plurality of pixel signals and converting the plurality of pixel signals to a digital positioning image;
    a memory storing positioning calibration information corresponding to an ideal three-dimensional position of the ophthalmic instrument relative to a calibration eye, wherein the positioning calibration information is based on a calibration location of the first source image and a calibration location of the second source image in a calibration image captured by the area detector when the ophthalmic instrument is at the ideal three-dimensional position relative to the calibration eye; and
    an image evaluation module configured to evaluate the digital positioning image to determine current positioning information corresponding to a current three-dimensional position of the ophthalmic instrument relative to the eye, wherein the current positioning information is based on a current location of the first source image and a current location of the second source image in the digital positioning image;
    wherein the image evaluation module is further configured to compare the current positioning information with the positioning calibration information stored in the memory and compute a position difference representing a difference between the current three-dimensional position of the ophthalmic instrument relative to the eye and the ideal three-dimensional position of the ophthalmic instrument relative to the calibration eye.

2. The ophthalmic instrument according to claim 1, wherein the first illumination axis and the second illumination axis are coplanar with the measurement axis and form an angle which is bisected by the measurement axis.

3. The ophthalmic instrument according to claim 2, wherein the first light source and the second light source fit within a lateral distance less than or equal to 25 mm.

4. The ophthalmic instrument according to claim 2, wherein the observation axis is coplanar with the measurement axis.

5. The ophthalmic instrument according to claim 4, wherein the first illumination axis and the second illumination axis are arranged in a horizontal plane containing the measurement axis, and the observation axis is arranged in a vertical plane containing the measurement axis.

6. The ophthalmic instrument according to claim 4, wherein the first illumination axis and the second illumination axis converge at a first point along the measurement axis within a field of view of the area detector, and the observation axis intersects the measurement axis at a second point along the measurement axis spaced from the first point.

7. The ophthalmic instrument according to claim 6, further comprising a working distance reference point on the measurement axis, wherein a distance between the working distance reference point and the second point is greater than a distance between the working distance reference point and the first point.

8. The ophthalmic instrument according to claim 1, wherein the first light source, the second light source, and the area detector are intersected by a plane which is normal to the measurement axis.

9. The ophthalmic instrument according to claim 1, further comprising a display connected to the image evaluation module, wherein the image evaluation module is further configured to generate a positioning icon representing the current three-dimensional position of the ophthalmic instrument relative to the eye, and to output the digital positioning image and the positioning icon to the display, wherein the digital positioning image and the positioning icon are superimposed to provide a positioning guidance image displayed on the display.

10. The ophthalmic instrument according to claim 9, wherein the positioning icon is scaled such that a size of the positioning icon is inversely proportional to a working distance of the ophthalmic instrument from the eye along the measurement axis.

11. The ophthalmic instrument according to claim 9, wherein an appearance attribute of the positioning icon is dependent upon whether or not the computed position difference is within a predetermined positioning tolerance for measurement purposes.

12. The ophthalmic instrument according to claim 1, wherein the ophthalmic instrument comprises a controller for initiating a measurement, wherein the image evaluation module is connected to the controller and is further configured to send a position confirmation signal to the controller when the computed position difference is within a predetermined positioning tolerance, and the controller automatically initiates the measurement in response to the position confirmation signal.

13. The ophthalmic instrument according to claim 1, wherein the ophthalmic instrument is a rebound tonometer which propels a probe along the measurement axis toward the eye or a non-contact tonometer which discharges a fluid pulse along the measurement axis toward the eye.

* * * * *